(12) United States Patent
Warngren (10) Patent No.: US 9,915,635 B1
(45) Date of Patent: Mar. 13, 2018

(54) COMPUTER PROGRAM, AN APPARATUS AND A METHOD FOR CORRECTING MEASURED LIGHT ABSORPTION VALUES IN CONNECTION WITH CHROMATOGRAPHY

(71) Applicant: Anders Warngren, Uppsala (SE)

(72) Inventor: Anders Warngren, Uppsala (SE)

(73) Assignee: BIOTAGE AB, Uppsala (SE)

( * ) Notice: Subject to any disclaimer, the term of this patent is extended or adjusted under 35 U.S.C. 154(b) by 444 days.

(21) Appl. No.: 13/833,248

(22) Filed: Mar. 15, 2013

(51) Int. Cl.
*G01N 30/78* (2006.01)
*G01N 30/86* (2006.01)

(52) U.S. Cl.
CPC ......... *G01N 30/8631* (2013.01); *G01N 30/78* (2013.01); *G01N 30/8624* (2013.01); *G01N 30/8644* (2013.01)

(58) Field of Classification Search
CPC .................. G01N 30/8624; G01N 30/8631
See application file for complete search history.

(56) References Cited

U.S. PATENT DOCUMENTS

| 4,802,102 A * | 1/1989 | Lacey ............... G06K 9/00503 702/32 |
| 7,312,246 B2 * | 12/2007 | Hamilton et al. ............ 514/533 |
| 2010/0238444 A1 * | 9/2010 | Anderson, Jr. ........ G01N 30/82 356/436 |
| 2011/0240841 A1 * | 10/2011 | Lange ................ H01J 49/0036 250/282 |

OTHER PUBLICATIONS

István, Krisztina, Róbert Rajkó, and Gábor Keresztury. "Towards the solution of the eluent elimination problem in high-performance liquid chromatography—infrared spectroscopy measurements by chemometric methods." Journal of Chromatography A 1104.1 (2006): 154-163.*

* cited by examiner

*Primary Examiner* — R. A. Smith
*Assistant Examiner* — Herbert K Roberts
(74) *Attorney, Agent, or Firm* — Harness, Dickey & Pierce PLC (57) ABSTRACT

The present invention relates to a computer program, an apparatus and a method for correcting light absorption values measured for an eluate in connection with performing chromatography on a chemical sample, the sample being eluted with an eluent having an eluent profile with changing solvent composition during the elution of the sample.

20 Claims, 7 Drawing Sheets

COMPUTER PROGRAM, AN APPARATUS AND A METHOD FOR CORRECTING MEASURED LIGHT ABSORPTION VALUES IN CONNECTION WITH CHROMATOGRAPHY

TECHNICAL FIELD

The present invention relates to an apparatus, a computer program and a method for correcting measured light absorption values for an eluate in connection with performing chromatography on a chemical sample.

PRIOR ART

Chromatography is a well-known procedure for analyzing chemical samples. In chromatography a chemical sample containing one or more compounds is made to migrate across a stationary phase (such as a solid material) by means of a mobile phase (such as a fluid flow). Depending on the polarity and structure of a compound forces may arise between the stationary phase and the compound resulting in that a fraction of the compound is adsorbed on the surface of the stationary phase while a remaining fraction reside in the mobile phase. Due to that this ratio differs between compounds, the compounds will be induced by a movement of the mobile phase to move at different speeds over the stationary phase and thus will become separated during an elution of the sample. According to standard procedure in liquid chromatography the eluted compounds are then detected by use of a light absorption technique, primarily ultra violet light absorption.

One problem with chromatography is that the solvents used in the eluent (the mobile phase) may also absorb light, meaning that any signals from compounds in the sample may be drowned by the signals of the solvents. One way of alleviating this problem is to make a baseline correction, wherein a known light absorption value for the eluent is removed from a measured light absorption value for the eluate.

In some cases of chromatography it is desired to change the composition of the eluent during the chromatography, a practice normally referred to as using a variable eluent profile or gradient eluent profile. In these cases the light absorption value for the eluent changes with the progression of the chromatographic run. Due to that the presence of a sample and other variable factors also affects the progression of the eluent it is difficult to predict when a gradient actually is eluted. It is therefore not an easy task to make a baseline correction in the same way as if the eluent had been constant. One known method for alleviating this problem is to calculate the derivative of a measured light absorption with respect to the progression of a chromatographic run, and to remove absorption values with a low derivative. This is based on the conjecture that the solvent composition varies only slowly, while an eluted compound of the sample is eluted under a limited time interval and thus is associated with a high absorption derivative. One problem with this method is that some compound peaks may be lost, especially if eluted in a region where the solvent composition has a high absorption, and that false artefact peaks may be introduced from the baseline correction, especially in the beginning of a solvent composition gradient.

SUMMARY OF THE INVENTION

One objective of the present invention is to achieve an improved correction of light absorption values in connection with performing chromatography of a sample.

Another objective is to achieve an improved correction of light absorption values in connection with performing chromatography of a sample when using an eluent having a solvent composition changing with the progression of a chromatographic run.

Another objective is to improve the ability to identify peaks in a light absorption spectrum obtained in connection with performing chromatography.

Another objective is to decrease the presence of artefacts or other perturbations in a corrected light absorption spectrum in connection with performing chromatography.

Another objective is to determine an improved fractionation of an eluate in connection with performing a chromatographic run.

In a first aspect of the invention at least one of these objectives is achieved with a computer program according to one of the corresponding independent claims. In a second aspect of the invention at least one of these objectives is achieved with an apparatus according to one of the corresponding independent claims. In a third aspect of the invention at least one of these objectives is achieved by a method according to one of the corresponding independent claims.

According to one embodiment the invention comprises correcting light absorption values measured on an eluate in connection with chromatography of a chemical sample, which chemical sample is eluted with an eluent having an eluent profile with changing solvent composition, the invention further comprising:

acquiring a plurality of eluent light absorption values comprising light absorption values measured for a plurality of different solvent compositions for the eluent and measured at a plurality of different wavelength sections of light, which solvent compositions are intended to be used in an eluent profile when eluting the sample, producing a light absorption correction factor associated with each wavelength section of said plurality of different wavelength sections of light based on said eluent light absorption values, acquiring a plurality of eluate light absorption values measured for the eluate at different moments of progression of a chromatographic run of the sample with said eluent profile and at said plurality of different wavelength sections of light, and correcting the eluate light absorption values for each wavelength section of said plurality of different wavelength sections of light individually by use of the light absorption correction factor produced for that specific wavelength section.

By correcting the eluate light absorption values for each wavelength section individually the quality of the corrected light absorption values is improved. For example, if a large correction is needed within one wavelength section, the correction will not spill over into another wavelength section, thus decreasing any negative effects from making the correction. This allows the use of more powerful corrections so as to allow easier identification of peaks, and simultaneously limits the effects of the powerful corrections, so as to avoid artefacts or involuntary removal of weak peaks. In particular, even though the solvent composition of the eluent changes over time the associated changes in the light absorption changes only within a limited number of wavelength sections, namely in those wavelength sections in which the solvents of the eluent absorb. Thus, by correcting each wavelength section individually, there is less errors introduced by the uncertainty in the eluent profile at different times or moments of progression of the chromatographic run.

In one embodiment the invention comprises correcting the eluate light absorption values for each moment of progression of the chromatographic run individually. By correcting the eluate light absorption values for each moment of the progression of the chromatographic run individually the negative impact on the corrected light absorption values from the variation in solvent compositions of the eluent decreases. Preferably, the invention comprises correcting the eluate light absorption values for each wavelength section and for each moment of progression of the chromatographic run individually. The procedure according to the invention thus results in a baseline correction that is split over several smaller wavelength sections and corrects the baseline in each wavelength section and for each moment of progression of the chromatographic run individually. By correcting the eluate light absorption values for both each wavelength section and for each moment of progression of the chromatographic run individually much improved, corrected light absorption values are achieved.

Further embodiments and advantages of the invention are shown in the following detailed description.

BRIEF DESCRIPTION OF THE ATTACHED DRAWINGS

The invention is now to be described as a number of non-limiting examples of the invention with reference to the attached drawings.

DETAILED DESCRIPTION

Figure 1:
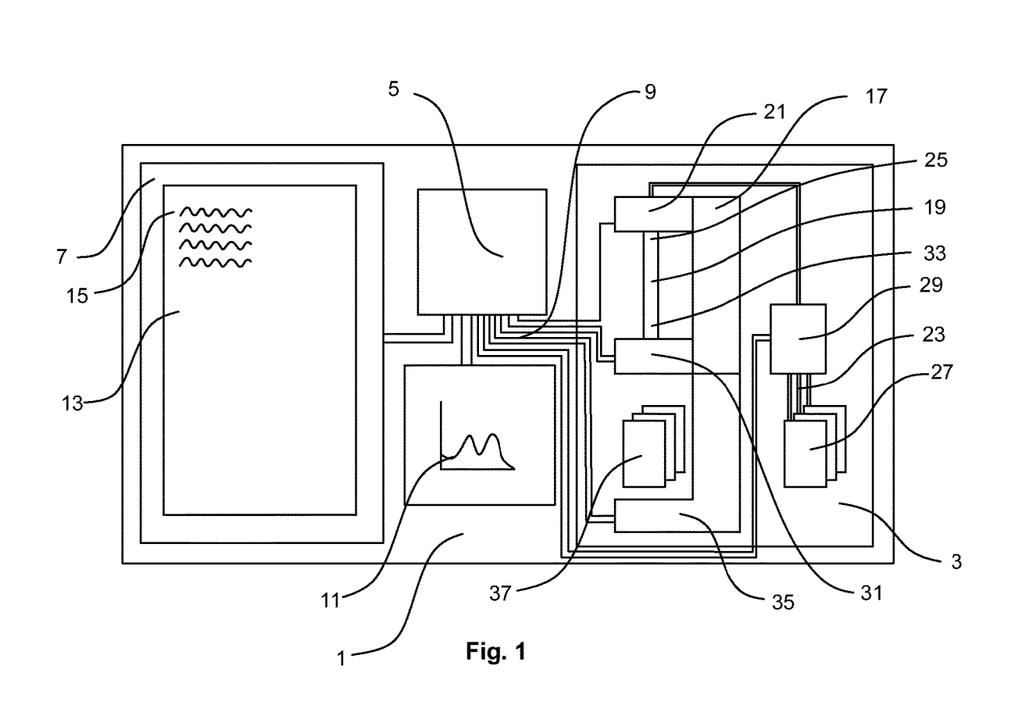
FIG. 1 shows an apparatus and a computer memory containing a computer program arranged to correct light absorption values measured for an eluate obtained during chromatography of a sample.

In FIG. 1 an apparatus arranged to correct light absorption values measured for an eluate obtained during chromatography of a chemical sample according to one example of the invention is shown. In this preferred example the apparatus 1 comprises a chromatograph 3 arranged to perform chromatography of the sample. The chromatograph is in this example a liquid chromatograph, using a liquid mobile phase. The chromatograph 3 is further designed for normal phase chromatography. In an alternative example, the apparatus could also be an apparatus separate from the chromatograph and arranged solely to process information obtained from a chromatograph located elsewhere, or the apparatus could be configured to be assembled to an existing chromatograph.

The apparatus 1 comprises a computer processor 5 (hereinafter termed processor), one or more computer memories 7, and at least one communication bus 9 arranged to communicate with input/output devices, in this example a touch screen 11, for receiving and presenting input/output to a user, and/or with external or internal technical devices. The one or more computer memories, which may comprise internal memory, such as chache memory, RAM-memory, flash memory and/or an internal or external hard disk memory or drive, further comprises a computer program stored therein, which is intended to be executed by the processor. The computer program comprises program instructions 15 arranged to induce the processor, and thus the apparatus, to perform a correction of eluate light absorption values according to the invention when executed, and/or to control the apparatus to perform such a correction. In this example, the inventive computer program 13 is also a control program for controlling the apparatus 1 to perform a chromatographic run as well as performing the inventive correction procedure. Alternatively, the computer program may be a patch mainly containing the program instructions for performing the inventive correction procedure, and which patch is designed to be patched into a control program for controlling a chromatographic run. In yet another alternative the program can be a separate program all together only designed to perform the correction procedure, and/or designed to communicate with a database or with a control program for controlling measurement of light absorption values and/or a chromatograph.

The chromatograph 3 contained in the apparatus 1 comprises a support 17 arranged to hold a chromatographic column 19, a sample loader 21 for loading a sample onto the column 19, one or more conductors (for liquid) 23 leading between an inlet 25 to the column and one or more containers 27 intended to hold solvents to be used in an eluent, and a flow generator 29 for inducing a flow of eluent to the column, such as one or more pumps. The chromatograph also comprises a light absorption detector 31, in this example a UV-light absorption detector, arranged downstream of an outlet 33 from the column to measure light absorption values on an eluate eluted from the column 19. The light absorption detector 31 is arranged to measure the light absorption in a plurality of different wavelength sections, and to give a light absorption measure in each wavelength section individually. In this example the chromatograph further comprises a fractionation device 35 arranged to automatically select and replace collection vessels 37 to receive the eluate eluted from the column.

The processor 5 of the apparatus is further arranged to communicate via the communication bus 9 with the different parts of the chromatograph 3, and in particular with the flow generator 29, the sample loader 21, the light absorption detector 31 and the fractionation device 35. The computer program is similarly designed to control the chromatograph 3 to perform the chromatography. The computer program is also designed to control the fractionation device 35 to fractionate an eluate in accordance with the corrected absorption values. In case the apparatus does not contain a chromatograph per se, then the apparatus and the computer program are preferably designed to correct eluate light absorption values originating from an external light absorption detector or chromatograph, preferably a liquid chromatograph, and preferably a normal phase chromatograph.

The nomenclature of this application follows IUPACs definitions unless otherwise stated. In particular, the following terms are adhered to: A chemical sample is a collection of known or unknown compounds of different constitutions and/or compositions. Chromatography is the separation of compounds in a chemical sample by letting the sample move across a stationary phase by using the flow of a mobile phase to move the compounds of the sample. An eluent is defined as a liquid forming the mobile phase used to elute the sample, and may comprise one or more solvents. A solvent is a liquid compound with the ability to dissolve, form colloids or form complexes with at least a part of the compounds in the sample. The stationary phase is normally provided in a column, and may comprise silica or some other polar material (termed normal phase chromatography), or an organic solid or some other non-polar material (termed reversed phase).

The progression of a chromatographic run is normally measured in terms of the number of or amounts of column volumes of eluent that has hitherto been applied onto the column. The progression could also be measured in time or some other suitable quantity. An eluent profile is the measure of the changing ratio of different solvents used in the eluent as applied onto a column at specific moments of progression of the chromatographic run. Hence, the solvent composition of the eluent may change during the chromatographic run. The eluate is defined as the substances that come out of the column. The components comprised in the eluate thus changes with the progression of the chromatographic run, and may thus comprise the solvents of the eluent and one or more compound(s) of the sample. Light absorption values are given as a ratio of the intensity of light absorbed when the light passes through a given distance of eluate relative to an irradiating intensity of light. It has no units, and is usually measured as values between 0 and 1. UV-light is here considered to be the wavelength range between 50 nm to 800 nm, and thus comprises a region of visible light as well (this is standard within the art).

According to the invention, the light absorption detector 31 is configured to be capable of measuring light absorption values at a plurality of different wavelength sections of light. In this example, the light absorption detector is configured to measure at least 100 different wavelength sections of light.

Preferably, the light absorption detector 31 is configured to measure at least 150 different wavelength sections of light. Preferably, the light absorption device 31 is configured to measure the different wavelength sections individually within the range of operation. It may be that two adjacent wavelength sections overlap to a small degree, but preferably every pair of adjacent wavelength sections 39 (FIG. 3) are disjoint. A wavelength section 39 is here defined as a smaller wavelength range, within which the light absorption detector measures and/or generates one single measurement value of light absorption. For example, the signal corresponding to one wavelength section could be measured by an individual sensor, or by an individual detector element within a sensor. Preferably, the measured light absorption values corresponding to a wavelength section is stored within one single data entry each, and the plurality of light absorption values for the plurality of wavelength sections are preferably stored in an array. The smallest possible wavelength section is given by Heisenberg's uncertainty relationship, but may be larger dependent on the design and resolution of the detector. Preferably, the light absorption detector 31 measures the different wavelength sections simultaneously. Preferably the light absorption detector 31 comprises a diode array detector which allows measurement of several wavelength sections simultaneously. Thus, the measured light absorption values comprise a plurality of values obtained at a plurality of different wavelength sections of light, and for each of a plurality of different moments of progression of the chromatographic run.

Figure 2:
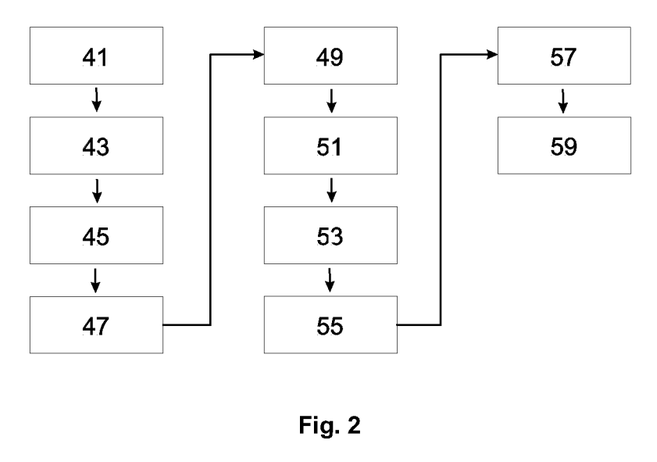
FIG. 2 shows one example of a method according to the invention.

In FIG. 2 there is shown an inventive method of operation performed by the computer program 13 and apparatus 1 according to the example in FIG. 1. In this preferred example the entire chromatographic sequence is included in the method, meaning that the computer program 13 and the apparatus 1 according to the invention control the chromatograph 3 and its operation. However, in another example the method, the computer program and apparatus may be designed to perform only the steps relating to the actual correction of the eluate light absorption values.

In a first, optional, step 41 of the preferred example of the method of operation, it comprises that the processor receives input values from a user or from communicating with technical parts of the chromatograph or apparatus. The information concerns the conditions and/or set-up of an intended chromatographic run of a chemical sample. The information may for example contain information on a desired eluent, in particular on a desired eluent profile comprising two or more different solvents, and the eluent's desired solvent compositions at different moments of progression of the chromatographic run. The information may further contain other information pertinent to the performing of a chromatographic run, such as a desired flow rate for the eluent, desired wavelength ranges for the measurement of light absorption, type of column, etc., and also possible supportive information such as information on an expected or guessed result of the elution of the sample, environmental factors such as temperature and other factors known to be pertinent to chromatography in the art.

In a second step 43 the method comprises initialising and performing a test chromatographic run using only the eluent, and to avoid introducing a sample. The computer program 13 and apparatus 1 are preferably designed to run the test chromatographic run automatically on receiving a start order from a user or similar. The program and apparatus then controls the chromatograph to perform the test chromatographic run with an eluent having an eluent profile of changing solvent compositions closely resembling a solvent composition profile of the eluent intended to be used when performing a subsequent real elution of the sample. The computer program and apparatus then controls the sample loader 21 to avoid loading the chemical sample onto the column, and controls the flow generator 29, such as pumps, to generate a flow of solvents of the eluent onto the column 19 in the desired ratio between the solvents to achieve the intended eluent profile and solvent compositions at different moments of progression of the test chromatographic run.

In a third step 45 the method comprises that the computer program 13, the processor 5 and/or the apparatus 1 controls the light absorption detector 31 to measure the light absorption values for the resulting eluate of the test chromatographic run at a plurality of different wavelength sections of light. The light absorption values for the resulting eluate of the test chromatographic run are further measured for a plurality of different moments of progression of the test chromatographic run. The resulting eluate achieved during the test chromatographic run comprises only the eluted eluent, and therefore the measured light absorption values are actually eluent light absorption values. Since the solvent composition of the eluent changes during the progression of the test chromatographic run the resulting eluent light absorption values correspond to different eluent solvent compositions.

Figure 3:
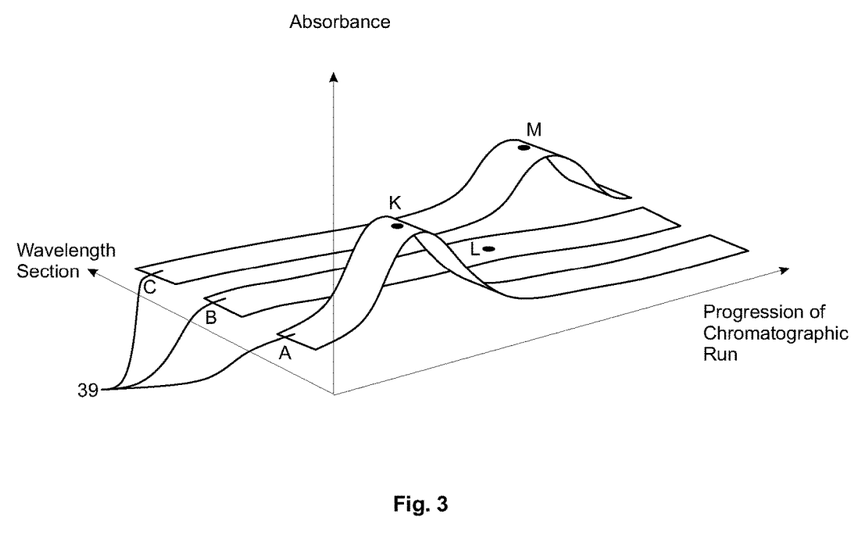
FIG. 3 shows a graph disclosing one example of a selection of a correction factor.

Thus the measured eluent light absorption values comprises a plurality of light absorption values measured for a plurality of different solvent compositions of the eluent and at a plurality of different wavelength sections of light. The method further comprises that the computer program 13 induces the processor 5 and apparatus 1 to acquire the measured eluent light absorption values from the light absorption detector 31. Preferably, the method also comprises storing the acquired eluent light absorption values into a data structure, such as a two-dimensional array, or matrix. In another example of the invention, the computer program, the processor, and/or the apparatus may instead acquire the eluent light absorption values from an external source and/or from a database of previously measured values. In a fourth step 47 the method comprises producing a light absorption correction factor associated with each wavelength section 39 of said plurality of different wavelength sections of light based on said eluent light absorption values. In one embodiment the method comprises producing a light absorption correction factor associated with each wavelength section of said plurality of different wavelength sections of light based on the eluent light absorption values measured at that wavelength section. According to a preferred embodiment the invention comprises selecting the maximum light absorption value from said eluent light absorption values for a wavelength section of light as the light absorption correction factor for that wavelength section. Since the solvent composition of the eluent changes during the progression of the chromatographic run the light absorption due to the eluent also changes. By selecting the maximum light absorption value that occurs during the chromatographic test run of the eluent in each wavelength section as basis for the correction factor, it is ensured that the correction will at least not be too small. Since the subsequent correction is made for each wavelength section individually the negative consequences of using a high level of correction at all times is substantially decreased. This effect is due to that the solvents in the eluent normally only absorbs light in a small wavelength range, and thus for only some of the wavelength sections. The fourth step further comprises that the computer program invoke a search algorithm to find the maximum light absorption value for the eluent in each wavelength section, and storing the maximum light absorption value in a correction factor array. One schematic example of the maximum light absorption value for each wavelength section is shown in FIG. 3. For wavelength section A the eluent composition has a strong absorption in the beginning of the test chromatographic run, in wavelength section B the eluent does not absorb at all, and in wavelength section C the eluent has a strong absorption at the end of the chromatographic run. Thus the light absorption values at points K, L and M are selected as the maximum light absorption values for sections A, B and C. The value at L is very low and will not disturb any peaks coming from compounds occurring in wavelength section B.

In this example the third and fourth steps are repeated continuously throughout, and for each moment of progression of, the test chromatographic run.

In a fifth step the method comprises that the computer program induces the processor 5 and the apparatus 1 to control the chromatograph 3 to perform a chromatographic run of the sample using an eluent profile having a changing solvent composition during the progression of the chromatographic run. The computer program thus induces the processor and the apparatus to control the sample loader to apply the sample onto the column, and the flow generator 29 to generate a flow of solvent in an appropriate ratio from the solvent containers to the column to establish a flow of mobile phase. During the chromatographic run the computer program induces the processor and the apparatus to control the light absorption detector to measure the light absorption of the eluate at a plurality of different wavelength sections of light and at a plurality of different moments of progression of the chromatographic run. The light absorption of the eluate is thus measured at evenly spaced moments throughout the entire chromatographic run. With the expression "each moment of progression . . . " is thus intended a finite sequence of points of time, where the time between two points or moments depends on the desired resolution for the absorption spectra and/or memory capacity. Further, the computer program induces the processor and the apparatus to acquire the measured light absorption values from the light absorption detector. In this example the acquired light absorption values are stored in a data structure, such as a two-dimensional array or matrix, with one dimension representing the different moments of progression of the chromatographic run and the other dimension the different wavelength sections of light.

In a sixth step the method comprises correcting the eluate light absorption values for each wavelength section of said plurality of different wavelength sections of light and for each moment of progression of the chromatographic run individually by use of the light absorption correction factor produced for that wavelength section. This gives the advantages as previously stated. In particular, the correction is performed so that the influence from the light absorption from the solvents in the eluent on the corrected light absorption values of the eluate is decreased. In a preferred embodiment the step of producing a corrected light absorption spectrum comprises subtracting the light absorption correction factor associated with each wavelength section of the plurality of wavelength sections of light from the acquired eluate light absorption value at that wavelength section. Thus the value of the correction factor for a wavelength section, which corresponds to the value of the light absorption for the solvents of the eluent in that wavelength section, is subtracted from the light absorption value for the eluate at that wavelength section. Since the subtraction is performed for each wavelength section individually the subtraction does not affect those wavelength sections in which the solvents of the eluents do not absorb, leading to that peaks in the other wavelength sections will not be affected.

In this example, since the value of the correction factor is given by the maximum absorption of the solvents in the eluent at that wavelength section, the subtraction of the correction factor removes all possible influence from the light absorption of the solvent. Thus it is ensured that all absorption originating from the solvents of the eluents is removed. In this example the method comprises that the computer program induces the processor and the apparatus to control the chromatograph to set the corrected light absorption value for the eluate for each wavelength section of the plurality of wavelength sections of light to zero in case the corresponding light absorption correction factor is greater than the corresponding acquired eluate light absorption value at that wavelength section. Thus there will not be any remnant negative values for those parts of the chromatographic run in which the absorption of the eluate is less than the maximum eluent absorption. To subtract the maximum eluent absorption is advantageous since it is difficult to know when the solvent composition changes to such a degree that the eluent light absorption begins to affect the measurement. By removing the maximum absorption all influence is always removed. Since the subtraction is done wavelength section for wavelength section, this practice does not give such a bad result as if it had been done for all wavelength sections taken as an aggregate whole, or if the light absorption values had been measured as only one value.

In this example the light absorption correction factor produced for a wavelength section of light is used to correct the eluate light absorption values for all moments of progression of the chromatographic run at that wavelength section. When eluting the eluent there are always some variations in how the eluent profile progress. Also, when including the sample the eluent may be affected, so that the eluted eluent profile will differ between when the sample is included or not. By this method according to the invention, there is no need to use derivatives of the eluate light absorption values to correct the values, meaning that less artefacts are introduced and that slowly changing peaks from compounds in the sample, or peaks from compounds with low absorption, are also detected.

Figure 4A:
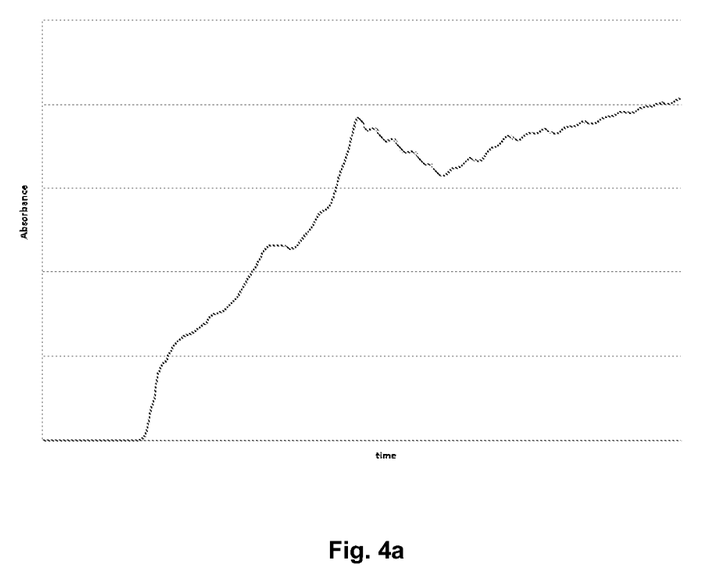
FIG. 4a shows a schematic, uncorrected absorption spectrum obtained from chromatography of a sample with a changing eluent profile.
Figure 4B:
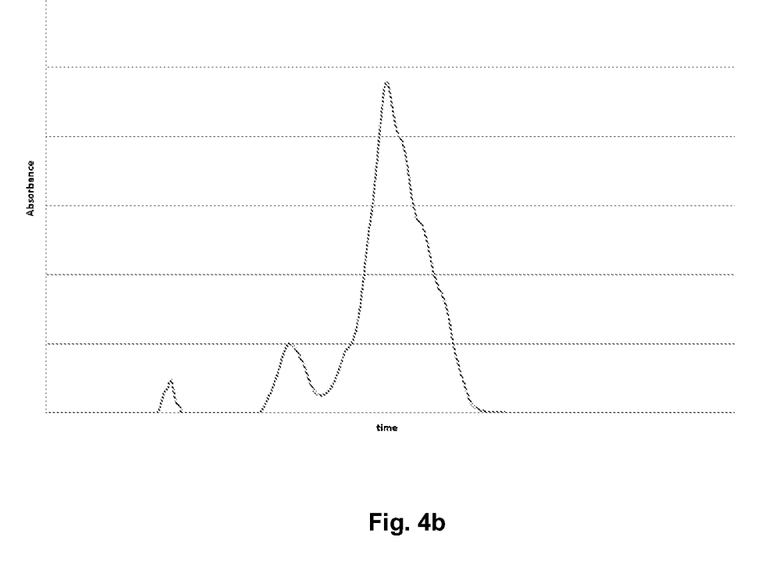
FIG. 4b shows a schematic absorption spectrum corrected according to the prior art.
Figure 4C:
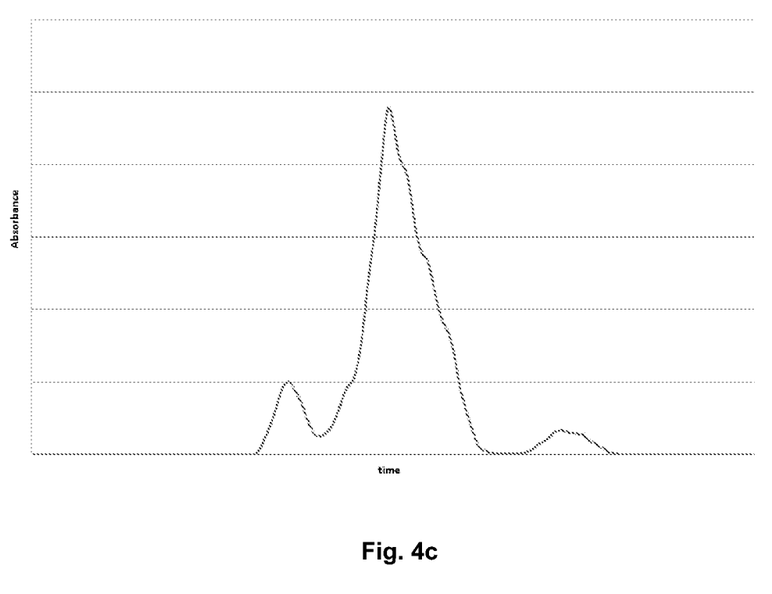
FIG. 4c shows a schematic absorption spectrum corrected according to the invention.

In a seventh step the method comprises, for each moment of progression of the chromatographic run, summing the corrected light absorption values for the plurality of wavelength sections of light at each moment of progression of the chromatographic run into an aggregated light absorption value for that moment of progression of the chromatographic run (FIG. 4c). Thus, an aggregate measurement value (or aggregate signal) is obtained reflecting the total light absorption for each moment of progression of the chromatographic run. The aggregate measurement value thus contains information about all measured peaks in all wavelength sections. This allows a joint evaluation of the possible presence of any compounds from the sample in the eluate. Since it is the corrected light absorption values that are summed, there is no contribution in the aggregate light absorption value at all from any light absorption of the solvents in the eluent.

In an eighth step the method comprises that the computer program 13 induces the processor 5 and/or the apparatus 1 to analyze the aggregated light absorption value during the progression of the chromatographic run so as to identify peaks in the aggregated light absorption value. The analyze step preferably comprises determining a fractionation of the eluate during the elution of the sample based on the identified peaks. For example a high, positive rate of change in the aggregated light absorption value with the progression of the chromatographic run may indicate that a peak corresponding to a compound of the sample is being eluted. Alternatively, a peak could be identified in case the aggregated light absorption value rises above a threshold value. The processor then determines that this part of the eluate should be collected in its own vessel, or in as few vessels as possible. By determining the fractionation based on the aggregated light absorption value a quick method giving at least a rough fractionation is achieved. Due to the inherent correction of the light absorption values due to the previous steps of the method a much better and finer fractionation is achieved than for previous prior art methods.

In a ninth step the method comprises that the computer program 13 induces the processor 5 and/or the apparatus 1 to control the fractionation device 29 to automatically perform a fractionation of the eluate so as to isolate the compounds shown as peaks in the aggregated light absorption values into vessels. Preferably, the computer program and processor in the apparatus controls the fractionation device so that the compounds of the sample are collected in as few vessels as possible, and so that the compounds are as concentrated as possible, with no or very small amounts of additional eluent in each vessel. The method thus comprises that the apparatus automatically fractionates the eluate by automaticaaly changing the collection vessels so as to isolate those compounds giving rise to peaks in as few collection vessels as possible.

In this example the fifth to ninth steps are repeated continuously for each moment of progression of the chromatographic run. Thus, the correction of the eluent absorption values is performed immediately as new light absorption measurement values are acquired from the light absorption detector. Similarly, the fractionation of the eluate is initiated immediately as soon as the analyzation of the aggregated light absorption values is concluded, and simultaneously with the progression of the chromatographic run.

Figure 4D:
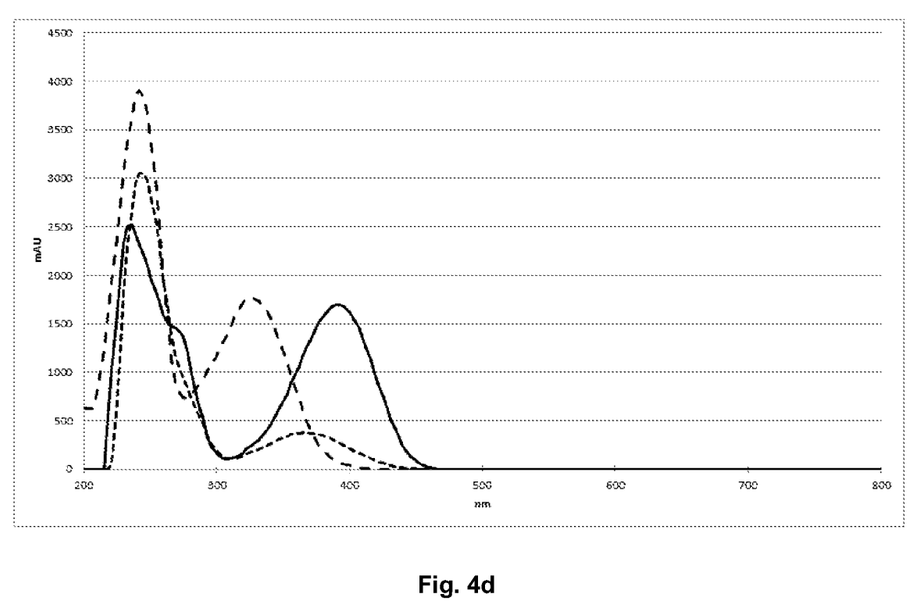
FIG. 4d shows one example of an absorption spectrum obtainable with the invention.

In a tenth step the method comprises presenting information on the various light absorption values to a user. In this example the invention comprises presenting the aggregated light absorption values as an aggregated light absorption spectrum as a function of the progression of the chromatographic run to a user. Such spectra are shown in FIGS. 4c-d. In this example the invention also comprises presenting the corrected (possibly also non-corrected) eluate light absorption values as a function of the different wavelength sections to a user at a moment of progression of the chromatographic run as selected by the user. In this example the invention also comprises presenting the corrected (possibly also non-corrected) eluate light absorption values as a function of the progression of the chromatographic run for a specific wavelength section. Alternatively the invention may comprise presenting the corrected eluate light absorption values in a three-dimensional spectrum, as a function of both the progression of the chromatographic run and of the wavelength sections of light simultaneously. Naturally, the presentation of the spectra also allows user input to control which spectrum, and/or which parts of a spectrum, to present.

In FIGS. 4a-d three examples of aggregated light absorption values as functions of the progression of a chromatographic run are shown to indicate the usefulness of the present invention. The spectra are simulations and not actual spectra. In FIG. 4a a raw aggregate spectrum without any corrections at all is shown. The spectrum thus shows the aggregate light absorption summed for all wavelength sections and containing the absorption of both the solvents of the eluent as well as for the compounds in the sample when eluted. As is seen the absorption from the solvents increases with changing solvent composition, and thus disturbs the visibility and possibilities of identifying the desired compound peaks in the spectrum.

In FIG. 4b a spectrum corrected in accordance with one method of the prior art is shown, in which the derivative of a single, aggregate signal measured over an entire wavelength range is used to correct the spectrum. Thus the slow changes in the signal as induced by the slowly changing solvent composition of the eluent are removed. However, in the beginning of the onset of the change an artefact peak is produced, before the method has time to realize that it is the solvent that produces the change in value and not a real peak of a compound. Similarly, the low peak C located in the region where the solvent absorption is high is removed, since the method is unable to discover slow changes. If using this aggregate spectrum to determine fractionation of the eluate, then there will be additional fractions collected due to the artefact, and the compound producing the peak C may become spread over several collection vessels, or be diluted by pouring too much eluate only containing solvent into the collection vessel or vessels containing the compound.

In FIG. 4c a simulated spectrum of an aggregate light absorption corresponding to the sum of corrected light absorption values of the eluate according to the invention is shown. As is evident there are no artefacts originating from the solvents of the eluent, and in fact the baseline is corrected so that the absorption signal from the eluent is completely removed, and only real peaks (B, C) corresponding to compounds in the sample are visible.

The invention is not limited to the examples and embodiments shown but may be varied freely within the framework of the following claims.

The invention claimed is:

1. An apparatus arranged to correct light absorption values obtained for an eluate in connection with performing chromatography of a chemical sample, wherein the sample is eluted with an eluent having an eluent profile with changing solvent composition during elution of the sample, the apparatus comprising at least one processor and an internal computer memory communicating with the processor and having a computer program stored therein, the computer program being arranged to cause the processor to perform the steps:

acquiring a plurality of eluent light absorption values for the eluent for a plurality of different solvent compositions of the eluent and a plurality of different wavelength sections of light, the plurality of eluent light absorption values including, for each given wavelength section of light of the plurality of different wavelength sections of light, a separate plurality of eluent light absorption values acquired at different moments of progression of a chromatographic test run of the eluent for the plurality of different wavelength sections of light, wherein the apparatus includes a particular plurality of light absorption detector elements that are each configured to individually measure a particular wavelength section having a particular width, such that a quantity of wavelength sections, of the plurality of different wavelength sections of light, is based on quantity of the plurality of light absorption detector elements of the apparatus, and a width of each wavelength section, of the plurality of different wavelength sections of light, is based on the plurality of light absorption detector elements of the apparatus, producing individual, time-independent light absorption correction factors associated with separate, respective wavelength sections of said plurality of different wavelength sections of light based on said eluent light absorption values, the producing including selecting, for each given wavelength section of light, only a maximum light absorption value from among the plurality of eluent light absorption values acquired at the different moments for the given wavelength section of light as the individual, time-independent light absorption correction factor associated with the given wavelength section of light, acquiring a plurality of eluate light absorption values for the eluate at different moments of progression of a chromatographic run of the sample with said eluent, the eluent having the eluent profile, and at said plurality of different wavelength sections of light, and correcting the eluate light absorption values for each wavelength section of said plurality of different wavelength sections of light, and for each moment of progression of the chromatographic run of the sample, based on the individual, time-independent light absorption correction factor associated with that specific wavelength section, the correcting performed individually for each wavelength section of the plurality of different wavelength sections of light based on the individual, time-independent light absorption correction factors associated with the separate, respective wavelength sections.

2. The apparatus of claim 1, wherein the producing further includes subtracting the light absorption correction factors associated with the wavelength sections of light from respective eluate light absorption values associated with the respective wavelength sections of light.

3. The apparatus of claim 1, the computer program further being arranged to cause the processor to set a corrected eluate light absorption value to zero, the corrected eluate light absorption value associated with a particular wavelength section of light and with a particular moment of progression of the chromatographic run, in response to the light absorption correction factor being greater than a corresponding eluate light absorption value, the corresponding eluate light adsorption value associated with the particular wavelength section of light and with the particular moment of progression of the chromatographic run.

4. An apparatus comprising a chromatograph arranged for chromatography of a chemical sample, at least one processor and an internal computer memory communicating with the processor and having a computer program stored therein, the computer program being arranged to cause the processor to:

acquire a plurality of eluent light absorption values comprising light absorption values measured for a plurality of different solvent compositions of the eluent and measured at a plurality of different wavelength sections of light, the plurality of solvent compositions associated with an eluent profile of the eluent, the plurality of eluent light absorption values including, for each given wavelength section of light of the plurality of different wavelength sections of light, a separate plurality of eluent light absorption values acquired at different moments of progression of a chromatographic test run of the eluent for the plurality of different wavelength sections of light, wherein the apparatus includes a particular plurality of light absorption detector elements that are each configured to individually measure a particular wavelength section having a particular width, such that a quantity of wavelength sections, of the plurality of different wavelength sections of light, is based on quantity of the plurality of light absorption detector elements of the apparatus, and a width of each wavelength section, of the plurality of different wavelength sections of light, is based on the plurality of light absorption detector elements of the apparatus, produce individual, time-independent light absorption correction factors associated with separate, respective wavelength sections of said plurality of different wavelength sections of light based on said eluent light absorption values, the producing including selecting, for each given wavelength section of light, only a maximum light absorption value from among the plurality of eluent light absorption values acquired at the different moments for the given wavelength section of light as the individual, time-independent light absorption correction factor associated with the given wavelength section of light, control the chromatograph to perform chromatography of the chemical sample, wherein the sample is eluted with the eluent, the eluent having the eluent profile with changing solvent composition during elution of the sample, acquire a plurality of eluate light absorption values measured for the eluate at different moments of progression of a chromatographic run of the sample with said eluent profile and at said plurality of different wavelength sections of light, and correct the eluate light absorption values for each wavelength section of said plurality of different wavelength sections of light, and for each moment of progression of the chromatographic run of the sample, based on the individual, time-independent light absorption correction factor associated with that specific wavelength section, the correcting performed individually for each wavelength section of the plurality of different wavelength sections of light based on the individual, time-independent light absorption correction factors associated with the separate, respective wavelength sections.

5. An apparatus according to claim 4, wherein the apparatus comprises a computer program arranged to cause the processor to:

perform a test chromatographic run using a test eluent with changing solvent composition resembling an eluent profile of an eluent intended for use in a real chromatography of the sample, measure test light absorption values for a resulting test eluate obtained in the test chromatographic run, and use the measured test light absorption values for the resulting test eluate in the test chromatographic run as said acquired eluent light absorption values.

6. A method for correcting light absorption values measured for an eluate in connection with performing chromatography of a chemical sample, wherein the sample is eluted with an eluent having an eluent profile with changing solvent composition during the elution of the sample, the method comprising:

acquiring, using a particular plurality of light absorption detector elements of an apparatus, a plurality of eluent light absorption values for the eluent for a plurality of different solvent compositions of the eluent and a plurality of different wavelength sections of light, the plurality of eluent light absorption values including, for each given wavelength section of light of the plurality of different wavelength sections of light, a separate plurality of eluent light absorption values acquired at different moments of progression of a chromatographic test run of the eluent for the plurality of different wavelength sections of light, wherein the light absorption detector elements are each configured to individually measure light absorption values for a particular wavelength section having a particular width, such that a quantity of wavelength sections, of the plurality of different wavelength sections of light, is based on a quantity of the plurality of light absorption detector elements of the apparatus, and a width of each wavelength section, of the plurality of different wavelength sections of light, is based on a corresponding light absorption detector element, of the plurality of light absorption detector elements of the apparatus, that is configured to measure light absorption values for the wavelength section, producing individual, time-independent light absorption correction factors associated with separate, respective wavelength sections of said plurality of different wavelength sections of light based on said eluent light absorption values, the producing including selecting, for each given wavelength section of light, only a maximum light absorption value from among the plurality of eluent light absorption values acquired at the different moments for the given wavelength section of light as the individual, time-independent light absorption correction factor associated with the given wavelength section of light, acquiring a plurality of eluate light absorption values for the eluate at different moments of progression of a chromatographic run of the sample with said eluent profile and at said plurality of different wavelength sections of light, and correcting the eluate light absorption values for each wavelength section of said plurality of different wavelength sections of light, and for each moment of progression of the chromatographic run of the sample, based on the individual, time-independent light absorption correction factor associated with that specific wavelength section, the correcting performed individually for each wavelength section of the plurality of different wavelength sections of light based on the individual, time-independent light absorption correction factors associated with the separate, respective wavelength sections.

7. The method of claim 6, wherein the producing further includes subtracting the light absorption correction factors associated with the wavelength sections of light from respective eluate light absorption values associated with the respective wavelength sections of light.

8. The method of claim 6, further comprising setting a corrected eluate light absorption value to zero, the corrected eluate light absorption value associated with a particular wavelength section of light and with a particular moment of progression of the chromatographic run, in response to the light absorption correction factor being greater than a corresponding eluate light absorption value, the corresponding eluate light adsorption value associated with the particular wavelength section of light and with the particular moment of progression of the chromatographic run.

9. A method for correcting light absorption values measured for an eluate in connection with performing chromatography of a chemical sample, wherein the sample is eluted with an eluent having an eluent profile with changing solvent composition during elution of the sample, the method comprising:

acquiring, using a particular plurality of light absorption detector elements of an apparatus, a plurality of eluent light absorption values comprising light absorption values measured for a plurality of different solvent compositions of the eluent and measured at a plurality of different wavelength sections of light, the plurality of solvent compositions associated with an eluent profile of the eluent, the plurality of eluent light absorption values including, for each given wavelength section of light of the plurality of different wavelength sections of light, a separate plurality of eluent light absorption values acquired at different moments of progression of a chromatographic test run of the eluent for the plurality of different wavelength sections of light, wherein the light absorption detector elements are each configured to individually measure light absorption values for a particular wavelength section having a particular width, such that a quantity of wavelength sections, of the plurality of different wavelength sections of light, is based on a quantity of the plurality of light absorption detector elements of the apparatus, and a width of each wavelength section, of the plurality of different wavelength sections of light, is based on a corresponding light absorption detector element, of the plurality of light absorption detector elements of the apparatus, that is configured to measure light absorption values for the wavelength section, producing individual, time-independent light absorption correction factors associated with separate, respective wavelength sections of said plurality of different wavelength sections of light based on said eluent light absorption values, the producing including selecting, for each given wavelength section of light, only a maximum light absorption value from among the acquired plurality of eluent light absorption values acquired at the different moments for the given wavelength section of light as the individual, time-independent light absorption correction factor associated with the given wavelength section of light, controlling a chromatograph to perform chromatography of the chemical sample, wherein the sample is eluted with the eluent, the eluent having the eluent profile with changing solvent composition during elution of the sample, acquiring a plurality of eluate light absorption values measured for the eluate at different moments of progression of a chromatographic run of the sample with said eluent profile and at said plurality of different wavelength sections of light, and correcting the eluate light absorption values for each wavelength section of said plurality of different wavelength sections of light, and for each moment of progression of the chromatographic run of the sample, based on the individual, time-independent light absorption correction factor associated with that specific wavelength section, the correcting performed individually for each wavelength section of the plurality of different wavelength sections of light based on the individual, time-independent light absorption correction factors associated with the separate, respective wavelength sections.

10. A method according to claim 9, wherein the method comprises:

performing a test chromatographic run using a test eluent with changing solvent composition resembling an eluent profile of an eluent intended for use in a real chromatography of the sample, measuring test light absorption values for a resulting test eluate obtained in the test chromatographic run, and using the measured test light absorption values for the resulting test eluate in the test chromatographic run as said acquired eluent light absorption values.

11. A non-transitory computer readable medium storing a program of instructions that, when executed by a computer system, cause the computer system to execute a method in association with performing chromatography of a chemical sample, the chromatography includes eluting the sample with an eluent having an eluent profile with changing solvent composition during elution of the sample, the method comprising:

acquiring, using a particular plurality of light absorption detector elements of an apparatus, a plurality of eluent light absorption values associated with the eluent for a plurality of different solvent compositions of the eluent and a plurality of different wavelength sections of light, the different solvent compositions are associated with the eluent profile of the eluent, the plurality of eluent light absorption values including, for each given wavelength section of light of the plurality of different wavelength sections of light, a separate plurality of eluent light absorption values acquired at different moments of progression of a chromatographic test run of the eluent for the plurality of different wavelength sections of light, wherein the light absorption detector elements are each configured to individually measure light absorption values for a particular wavelength section having a particular width, such that a quantity of wavelength sections, of the plurality of different wavelength sections of light, is based on a quantity of the plurality of light absorption detector elements of the apparatus, and a width of each wavelength section, of the plurality of different wavelength sections of light, is based on a corresponding light absorption detector element, of the plurality of light absorption detector elements of the apparatus, that is configured to measure light absorption values for the wavelength section, producing individual, time-independent light absorption correction factors associated with separate, respective wavelength sections of the plurality of different wavelength sections of light based on the plurality of eluent light absorption values, the producing including selecting, for each given wavelength section of light, only a maximum light absorption value from among the plurality of eluent light absorption values acquired at the different moments for the given wavelength section of light as the individual, time-independent light absorption correction factor associated with the given wavelength section of light, acquiring a plurality of eluate light absorption values for an eluate at different moments of progression of a chromatographic run of a chemical sample with the eluent, the eluent having the eluent profile, and at said plurality of different wavelength sections of light, and correcting a plurality of measured eluate light absorption values for each wavelength section of said plurality of different wavelength sections of light, and for each moment of progression of the chromatographic run of the sample, based on the individual, time-independent light absorption correction factor associated with the respective wavelength section, the correcting performed individually for each wavelength section of the plurality of different wavelength sections of light based on the individual, time-independent light absorption correction factors associated with the separate, respective wavelength sections.

12. The non-transitory computer readable medium of claim 11, wherein the producing further includes subtracting the light absorption correction factors associated with the wavelength sections of light from respective eluate light absorption values associated with the respective wavelength sections of light.

13. The non-transitory computer readable medium of claim 11, the method further comprising individually correcting the eluate light absorption values for each moment of progression of the chromatographic run and for each wavelength section of said plurality of different wavelength sections of light.

14. The non-transitory computer readable medium of claim 11, the method further comprising setting a corrected eluate light absorption value to zero, the corrected eluate light absorption value associated with a particular wavelength section of light and with a particular moment of progression of the chromatographic run, in response to the light absorption correction factor being greater than a corresponding eluate light absorption value, the corresponding eluate light adsorption value associated with the particular wavelength section of light and with the particular moment of progression of the chromatographic run.

15. The non-transitory computer readable medium of claim 11, the method further comprising, for each moment of progression of the chromatographic run, summing a plurality of corrected light absorption values associated with the plurality of wavelength sections of light at that moment of progression of the chromatographic run into an aggregated light absorption value associated with that moment of progression of the chromatographic run.

16. The non-transitory computer readable medium of claim 15, the method further comprising:
    analysing the aggregated light absorption value during elution of the sample so as to identify peaks in the aggregated light absorption value, and
    determining a fractionation of the eluate during the progression of the chromatographic run based on the identified peaks.

17. The non-transitory computer readable medium of claim 11, wherein the plurality of wavelength sections of light comprises at least 100 different wavelength sections.

18. The non-transitory computer readable medium of claim 11, the method further comprising acquiring the plurality of eluent light absorption values as measured test light absorption values measured on a resulting test eluate obtained from a test chromatographic run.

19. A non-transitory computer readable medium storing a program of instructions that, when executed by a computer system, cause the computer system to execute a method for correcting light absorption values measured for an eluate in connection with performing chromatography of a chemical sample, the chromatography includes eluting the sample with an eluent having an eluent profile with changing solvent composition during elution of the sample, the method comprising:
    acquiring, using a particular plurality of light absorption detector elements of an apparatus, a plurality of eluent light absorption values comprising light absorption values measured for a plurality of different solvent compositions of the eluent and measured at a plurality of different wavelength sections of light, the plurality of solvent compositions associated with the eluent profile, the plurality of eluent light absorption values including, for each given wavelength section of light of the plurality of different wavelength sections of light, a separate plurality of eluent light absorption values acquired at different moments of progression of a chromatographic test run of the eluent for the plurality of different wavelength sections of light, wherein the light absorption detector elements are each configured to individually measure light absorption values for a particular wavelength section having a particular width, such that
        a quantity of wavelength sections, of the plurality of different wavelength sections of light, is based on a quantity of the plurality of light absorption detector elements of the apparatus, and
        a width of each wavelength section, of the plurality of different wavelength sections of light, is based on a corresponding light absorption detector element, of the plurality of light absorption detector elements of the apparatus, that is configured to measure light absorption values for the wavelength section,
    producing individual, time-independent light absorption correction factors associated with separate, respective wavelength sections of said plurality of different wavelength sections of light based on said eluent light absorption values, the producing including selecting, for each given wavelength section of light, only a maximum light absorption value from among the plurality of eluent light absorption values acquired at the different moments for the given wavelength section of light as the individual, time-independent light absorption correction factor associated with the given wavelength section of light,
    controlling a chromatograph to perform chromatography of the sample, wherein the sample is eluted with the eluent, the eluent having the eluent profile with changing solvent composition during the elution of the sample,
    acquiring a plurality of eluate light absorption values measured for the eluate at different moments of progression of a chromatographic run of the sample with said eluent profile and at said plurality of different wavelength sections of light, and
    correcting the eluate light absorption values for each wavelength section of said plurality of different wavelength sections of light, and for each moment of progression of the chromatographic run of the sample, individually by use of the individual, time-independent light absorption correction factor associated with that specific wavelength section, the correcting performed individually for each wavelength section of the plurality of different wavelength sections of light based on the individual, time-independent light absorption correction factors associated with the separate, respective wavelength sections.

20. The non-transitory computer readable medium of claim 19, wherein the method further comprises:
    controlling the chromatograph to perform a test chromatographic run using a test eluent with changing solvent composition resembling the eluent profile of the eluent,
    acquiring test light absorption values for a resulting test eluate obtained in the test chromatographic run, and
    using the test light absorption values for the resulting test eluate in the test chromatographic run as said eluent light absorption values.

* * * * *